(12) United States Patent
Chang et al.

(10) Patent No.: US 11,760,853 B2
(45) Date of Patent: Sep. 19, 2023

(54) ANTI-CURLING FILM

(71) Applicant: INDUSTRIAL TECHNOLOGY RESEARCH INSTITUTE, Hsinchu (TW)

(72) Inventors: Wei-Hong Chang, Linnei Township (TW); Ching-Mei Chen, Tainan (TW); Grace H. Chen, Zhubei (TW); Hsin-Hsin Shen, Taipei (TW); Yuchi Wang, New Taipei (TW); Ming-Chia Yang, Zhudong Township (TW); Li-Hsin Lin, Zhubei (TW); Sen-Lu Chen, Zhunan Township (TW); Yi-Hsuan Lee, Taipei (TW); Jian-Wei Lin, Tainan (TW); Liang-Cheng Su, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 141 days.

(21) Appl. No.: 17/537,728

(22) Filed: Nov. 30, 2021

(65) Prior Publication Data
US 2022/0169808 A1 Jun. 2, 2022

Related U.S. Application Data

(60) Provisional application No. 63/119,354, filed on Nov. 30, 2020.

(30) Foreign Application Priority Data

Nov. 15, 2021 (TW) .................. 110142436

(51) Int. Cl.
| | | |
|---|---|---|
| C08J 5/18 | (2006.01) | |
| A61L 24/04 | (2006.01) | |
| B32B 27/36 | (2006.01) | |
| B32B 9/02 | (2006.01) | |
| B32B 9/04 | (2006.01) | |

(52) U.S. Cl.
CPC .............. C08J 5/18 (2013.01); A61L 24/043 (2013.01); B32B 9/02 (2013.01); B32B 9/045 (2013.01); B32B 27/36 (2013.01); C08J 2335/02 (2013.01)

(58) Field of Classification Search
CPC ................................................ A61L 15/225
See application file for complete search history.

(56) References Cited

U.S. PATENT DOCUMENTS

| | | |
|---|---|---|
| 8,383,092 B2 | 2/2013 | Lee et al. |
| 8,703,176 B2 | 4/2014 | Zhu et al. |
| 9,320,826 B2 | 4/2016 | Lee et al. |
| 10,729,715 B2 | 8/2020 | Cooper et al. |
| 11,154,637 B2 | 10/2021 | Shen et al. |
| 2007/0280990 A1 | 12/2007 | Stopek |
| 2018/0200403 A1 | 7/2018 | Chang et al. |
| 2019/0343980 A1 | 11/2019 | Gittard et al. |
| 2020/0247101 A1 | 6/2020 | Shen et al. |
| 2020/0254136 A1 | 8/2020 | Liu et al. |

FOREIGN PATENT DOCUMENTS

| | | |
|---|---|---|
| CN | 105496566 A | 4/2016 |
| CN | 108210986 A | 6/2018 |
| CN | 108888798 A | 11/2018 |
| CN | 111150878 A | 5/2020 |
| CN | 111150888 A | 5/2020 |
| EP | 1 812 022 B1 | 1/2014 |
| JP | 2008-31296 A | 2/2008 |
| TW | I652076 B | 3/2019 |
| TW | 202017991 A | 5/2020 |
| WO | WO 2006/102457 A2 | 9/2006 |
| WO | WO 2009/056288 A2 | 5/2009 |
| WO | WO 2009/079645 A2 | 6/2009 |
| WO | WO 2009/091549 A1 | 7/2009 |

OTHER PUBLICATIONS

Chinese Office Action for Appl. No. 202111443633.6 dated Aug. 3, 2022.
Chuang et al., "A novel technique to apply Seprafilm (hyaluronate-carboxymethylcellulose) barrier following laparoscopic surgeries," Fertility and Sterility, vol. 90, No. 5, Nov. 2008, pp. 1959-1963.
Chuang et al., "Modified novel technique to improve success rate of applying Seprafilm by laparoscopy," The Journal of Minimally Invasive Gynecology, 2014, 30 pages total.
Fairbanks et al., "Photoinitiated polymerization of PEG-diacrylate with lithium phenyl-2,4,6-trimethylbenzoylphosphinate: polymerization rate and cytocompatatbility," Biomaterials, vol. 30, 2009 (Available online Sep. 23, 2009), pp. 6702-6707.
Hammond et al., "The Burden of Gastrointestinal Anastomotic Leaks: an Evaluation of Clinical and Economic Outcomes," J Gastrointest Surg, vol. 18, 2014 (Available online Mar. 27, 2014), pp. 1176-1185.
Hong et al., "Seprafilm Application Method in Laparoscopic Surgery," JSLS, vol. 21, Issue 1, Jan.-Mar. 2017, pp. 1-5.
Mironi-Harpaz et al., "Photopolymerization of cell-encapsulating hydogels: Crosslinking efficiency versus cytotoxicity," Acta Biomaterialia, vol. 8, 2012 (Available online Jan. 13, 2012), pp. 1838-1848.
Extended European Search Report for corresponding European Application No. 21211426.8, dated Apr. 26, 2022.
Zhang et al., "In Situ Formation of Blends by Photopolymerization of Poly(ethylene glycol) Dimethacrylate and Polylactide," Biomacromolecules, vol. 6, 2005 (Published online Apr. 2, 2005), pp. 1615-1622.

*Primary Examiner* — Jeffrey C Mullis
(74) *Attorney, Agent, or Firm* — Birch, Stewart, Kolasch & Birch, LLP

(57) ABSTRACT

An anti-curling film is provided. The anti-curling film includes a first portion and a second portion covering the first portion. The first portion includes polylactic acid (PLA), polycaprolactone (PCL), polyethylene glycol dimethacrylate (PEGDMA) and a photoinitiator. The second portion includes polycaprolactone (PCL), gelatin, hyaluronic acid (HA), alginate (AA), polyvinyl alcohol (PVA) or a combination thereof.

23 Claims, 9 Drawing Sheets

ANTI-CURLING FILM

CROSS REFERENCE TO RELATED APPLICATIONS

This non-provisional application claims the benefit under 35 U.S.C. § 119(e) to U.S. Provisional Application No. 63/119,354, filed on Nov. 30, 2020, and under 35 U.S.C. § 119(a) to patent application Ser. No. 11/014,2436, filed in Taiwan on Nov. 15, 2021, all of which are hereby expressly incorporated by reference into the present application.

TECHNICAL FIELD

The present disclosure is related to an anti-curling film.

BACKGROUND

At present, the adhesive and water-absorbent film used in clinical practice often causes the material to melt and collapse due to the absorption of a large amount of tissue fluid, or the film warps and detaches due to volume swelling, which causes difficulties in clinical use, makes the treatment accuracy low, or even invalid.

The current solutions in common use include the use of water-absorbent or hydrophobic polymers alone. In addition, due to the characteristics of the material itself which cause it to warp easily, most of the materials can only be used on specific organs, which makes for poor clinical operability, and the production process and related verification of the product incur high costs and low market acceptance.

Therefore, it is expected that a film that can avoid warping during the process of attaching it to tissues will be developed.

SUMMARY

In the clinical patching of wounds, the clinical surgical film often absorbs a large amount of tissue fluid during the process of being attached to an organ. This makes the film swell and warp, resulting in poor clinical operability. Even the structure can be damaged by the swelling, and the film and the tissue surface may become detached, which reduces the therapeutic effect.

In accordance with one embodiment of the present disclosure, an anti-curling film is provided. The anti-curling film includes a first portion and a second portion covering the first portion. The first portion includes polylactic acid (PLA), polycaprolactone (PCL), polyethylene glycol dimethacrylate (PEGDMA) and a photoinitiator. The second portion includes polycaprolactone (PCL), gelatin, hyaluronic acid (HA), alginate (AA), polyvinyl alcohol (PVA) or a combination thereof.

In some embodiments, the grafting rate of polyethylene glycol dimethacrylate (PEGDMA) is between 65% and 72%.

In some embodiments, the weight ratio of polylactic acid (PLA), polycaprolactone (PCL) and polyethylene glycol dimethacrylate (PEGDMA) is between 0.5:1:1 and 0.5:1:6.

In some embodiments, the first portion includes a first layer and a second layer. In some embodiments, the first layer includes polycaprolactone (PCL) and polyethylene glycol dimethacrylate (PEGDMA), and the weight ratio of polycaprolactone (PCL) to polyethylene glycol dimethacrylate (PEGDMA) is between 1:6 and 1:12. In some embodiments, the second layer includes polyethylene glycol dimethacrylate (PEGDMA) and polylactic acid (PLA), and the weight ratio of polyethylene glycol dimethacrylate (PEGDMA) to polylactic acid (PLA) is between 1:1 and 3:1.

In some embodiments, the weight ratio of polyethylene glycol dimethacrylate (PEGDMA), polylactic acid (PLA) and the photoinitiator is between 1:1:0.005 and 3:1:0.015. In some embodiments, the weight ratio of polylactic acid (PLA), polycaprolactone (PCL), polyethylene glycol dimethacrylate (PEGDMA) and the photoinitiator is between 2:1:7:0.03 and 3:1:12:0.06. In some embodiments, when the content of polyethylene glycol dimethacrylate (PEGDMA) is too low, the film cannot be formed. In some embodiments, when the content of polyethylene glycol dimethacrylate (PEGDMA) is too high, it will affect the bonding effect of the overall film and the tissue. In some embodiments, if the weight ratio of the photoinitiator is too low, it will affect the bonding effect of the overall film and the tissue. If the weight ratio of the photoinitiator is too high, it is easy to produce toxicity and cause tissue inflammation. In some embodiments, when the weight ratio of polycaprolactone (PCL) is too low, it may affect film formation, or when the weight ratio of polycaprolactone (PCL) is too high, the film will lose the adhesion effect because the functional groups for attachment are embedded in the PCL polymer.

In some embodiments, the second portion includes a first layer and a second layer. In some embodiments, the first layer includes polycaprolactone (PCL), gelatin, alginate (AA) or a combination thereof. In some embodiments, the second layer includes polycaprolactone (PCL), hyaluronic acid (HA), polyvinyl alcohol (PVA) or a combination thereof. In some embodiments, the first layer includes polycaprolactone (PCL) and gelatin, and the weight ratio of polycaprolactone (PCL) to gelatin is between 0.14:1 and 1:1. In some embodiments, the first layer includes polycaprolactone (PCL) and alginate (AA), and the weight ratio of polycaprolactone (PCL) to alginate (AA) is between 8:1 and 4:1. In some embodiments, the first layer includes polycaprolactone (PCL), gelatin and alginate (AA), and the weight ratio of polycaprolactone (PCL), gelatin and alginate (AA) is between 1:1:0.1 and 1:1.85:0.125. In some embodiments, the first layer includes alginate (AA), and the weight percentage of alginate (AA) is between 1 wt % and 5 wt %. In some embodiments, the second layer includes polycaprolactone (PCL) and hyaluronic acid (HA), and the weight ratio of polycaprolactone (PCL) to hyaluronic acid (HA) is between 10:1 and 35:1. In some embodiments, the second layer includes polycaprolactone (PCL) and polyvinyl alcohol (PVA), and the weight ratio of polycaprolactone (PCL) to polyvinyl alcohol (PVA) is between 1:0.1 and 1:0.16. In some embodiments, the second layer includes polycaprolactone (PCL), hyaluronic acid (HA) and polyvinyl alcohol (PVA), and the weight ratio of polycaprolactone (PCL), hyaluronic acid (HA) and polyvinyl alcohol (PVA) is between 10:1:0.5 and 35:1:1. In some embodiments, when the content of gelatin and alginate (AA) in the second portion is too low, although the tissue fluid on the surface of the tissue can be quickly absorbed, the second portion is easily dissolved by the tissue fluid and cannot maintain its stable structure (i.e. the second portion is easily washed away by the tissue fluid, which reduces the repair/attachment time to the surface of the organ, and loses the function of protection, causing the film to warp again). In some embodiments, when the content of gelatin and alginate (AA) in the second portion is too high, after the film is formed, the material is hard due to the high polymer content, so the polymer cannot quickly absorb the tissue fluid in a short time during operation (i.e. the intermolecular space is relatively dense, and water molecules such as tissue fluid take a long time to enter), which reduces the effect of absorbing tissue fluid, and it is easy to cause warpage when the film is attached to the tissue. Due to the high polymer content, the long-term absorption of the tissue will also lead to excessive swelling and excessive thickness. Warpage and excessive thickness can easily cause the film to peel off or slip due to tissue peristalsis and lose the adhesion effect, and the protective effect cannot be achieved. In some embodiments, after the second portion absorbs tissue fluid, it can remain on the surface of the tissue for 24-48 hours without being washed away by the body fluid.

In some embodiments, the second portion includes gelatin and alginate (AA), or gelatin. In some embodiments, the second portion includes gelatin and alginate (AA), and the weight ratio of gelatin to alginate (AA) is between 4:1 and 14.5:1. In some embodiments, the second portion includes gelatin, and the weight percentage of gelatin is between 10 wt % and 29.9 wt %.

In some embodiments, the area ratio of the first portion to the second portion is between 5:100 and 65:100.

In accordance with one embodiment of the present disclosure, an anti-curling film is provided. The anti-curling film includes the second portion of the disclosed anti-curling film.

The present disclosure aims at the film material with tissue attachment and water absorption (hydrophilic) (the light-cured layer—the first portion of the anti-curling film), using a protective manner (covered by the protective layer—the second portion of the anti-curling film) to produce a specific area ratio with the film material to limit the water absorption when the absorbent film is attached to the tissue surface (for example, liver, gastrointestinal tract, etc.). When the water-absorbent film is used clinically and attached to the surface of the internal organs of the body, it can effectively reduce the phenomenon of warping caused by the swelling of the volume of the water-absorbent film due to the absorption of a large amount of tissue fluid, and it can also effectively avoid the occurrence of detachment between the film material and the tissue surface due to warping.

The present disclosure is mainly to solve the warping condition caused by the water absorption of the film. The specific area ratio between the film layers is used to effectively control the water absorption state of the film and reduce the water absorption efficiency in the process of attaching to the tissue. Also, the design of light-sensitive curing is combined in the material, and the UV light of a fixed wavelength is irradiated to strengthen the attachment effect of the film to the surface of the tissue, so that while the UV light promotes the attachment speed of the film, the polymer material rearranges the molecules under the condition of reducing water absorption, which reduces the generation of warping stress in the film, thereby eliminating the occurrence of warping.

A detailed description is given in the following embodiments with reference to the accompanying drawings.

DETAILED DESCRIPTION

Figure 1:
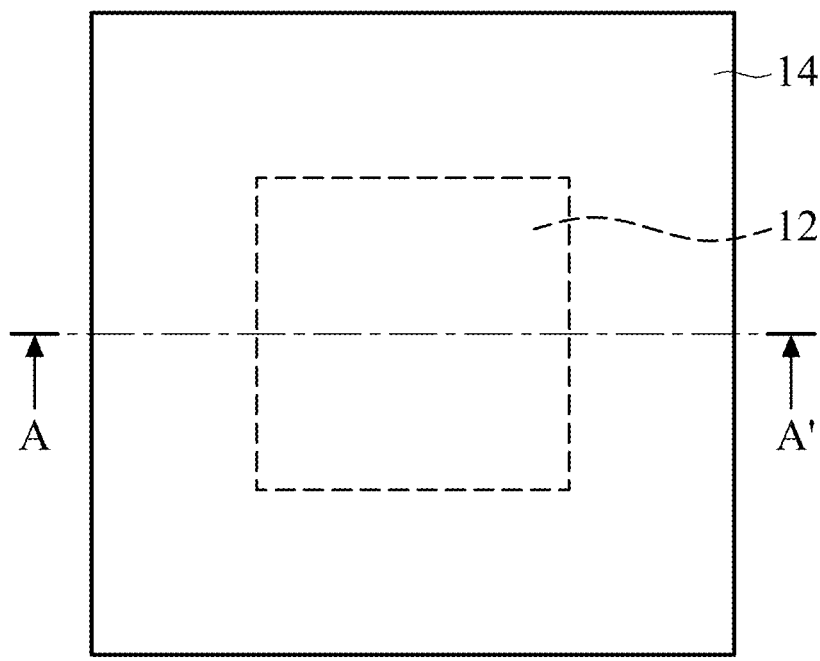
FIG. 1 is a top view of an anti-curling film in accordance with one embodiment of the present disclosure.
Figure 2:
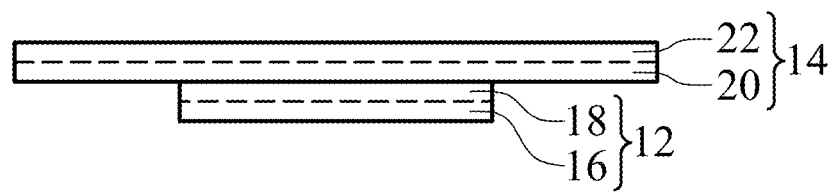
FIG. 2 is a cross-sectional view of an anti-curling film taken along the line A-A' in FIG. 1 in accordance with one embodiment of the present disclosure.

Referring to FIGS. 1 and 2, in accordance with one embodiment of the present disclosure, an anti-curling film 10 is provided. FIG. 1 is the top view of the anti-curling film 10. FIG. 2 is a cross-sectional view taken along the line A-A' in FIG. 1.

As shown in FIGS. 1 and 2, the anti-curling film 10 includes a light-cured layer 12 and a protective layer 14. The protective layer 14 covers the light-cured layer 12. The term "cover" here means, from the top view or cross-sectional view, the light-cured layer 12 underneath does not exceed the scope of the upper protective layer 14. The light-cured layer 12 includes polylactic acid (PLA), polycaprolactone (PCL) and polyethylene glycol dimethacrylate (PEGDMA).

In the embodiment shown in FIGS. 1 and 2, the light-cured layer 12 is a double layer. For example, the light-cured layer 12 includes a first layer 16 and a second layer 18, but the present disclosure is not limited thereto. In some embodiments, the first layer 16 includes polycaprolactone (PCL) and polyethylene glycol dimethacrylate (PEGDMA), and the weight ratio of polycaprolactone (PCL) to polyethylene glycol dimethacrylate (PEGDMA) is between about 1:6 and about 1:12. When the weight ratio of polycaprolactone (PCL) to polyethylene glycol dimethacrylate (PEGDMA) is too low (for example, less than 1:6), the configuration of the first layer 16 will not be formed. If the weight ratio is too high (for example, higher than 1:12), the first layer 16 will be separated from the second layer 18 and cannot be effectively combined. In some embodiments, the second layer 18 includes polyethylene glycol dimethacrylate (PEGDMA) and polylactic acid (PLA), and the weight ratio of polyethylene glycol dimethacrylate (PEGDMA) to polylactic acid (PLA) is between about 1:1 and about 3:1. When the weight ratio of polyethylene glycol dimethacrylate (PEGDMA) to polylactic acid (PLA) is too low (for example, less than 1:1), the configuration of the second layer 18 cannot be formed. If the weight ratio is too high (for example, higher than 3:1), the second layer 18 cannot be effectively combined with the first layer 16.

In some embodiments, the light-cured layer 12 is a single layer. For example, the light-cured layer 12 includes polylactic acid (PLA), polycaprolactone (PCL) and polyethylene glycol dimethacrylate (PEGDMA). In some embodiments, the weight ratio of polylactic acid (PLA), polycaprolactone (PCL) and polyethylene glycol dimethacrylate (PEGDMA) is between about 0.5:1:1 and about 0.5:1:6 in the light-cured layer 12. When the weight ratio of the aforementioned three raw materials is based on PCL, if the ratio range of PLA to PEGDMA is lower than the above ratio, the light-cured layer may not be effectively formed into a film and cause cracking and damage. If the ratio range is higher than the above ratio, the photocuring effect may be reduced, or even failure may occur. In another situation, if the weight percentage of PEGDMA in the light-cured layer exceeds the weight percentage of PCL and PLA by more than 50%, the light-cured layer may not be effectively formed, resulting in film damage and process failure.

In the embodiment shown in FIGS. 1 and 2, the light-cured layer 12 further includes a photoinitiator, for example, Irgacure 2959, Irgacure 819 DW or Irgacure 127. In some embodiments, the weight ratio of polyethylene glycol dimethacrylate (PEGDMA), polylactic acid (PLA) and the photoinitiator is between about 1:1:0.005 and about 3:1:0.015. In some embodiments, the weight ratio of polylactic acid (PLA), polycaprolactone (PCL), polyethylene glycol dimethacrylate (PEGDMA) and the photoinitiator is between about 2:1:7:0.03 and about 3:1:12:0.06.

In the embodiment shown in FIGS. 1 and 2, the protective layer 14 is a double layer. For example, the protective layer 14 includes a first layer 20 and a second layer 22, but the present disclosure is not limited thereto. In some embodiments, the first layer 20 includes polycaprolactone (PCL), gelatin, alginate (AA) or a combination thereof. In some embodiments, the second layer 22 includes polycaprolactone (PCL), hyaluronic acid (HA), polyvinyl alcohol (PVA) or a combination thereof. In some embodiments, the first layer includes polycaprolactone (PCL) and gelatin, and the weight ratio of polycaprolactone (PCL) to gelatin is between about 0.14:1 and about 1:1. In some embodiments, the first layer includes polycaprolactone (PCL) and alginate (AA), and the weight ratio of polycaprolactone (PCL) to alginate (AA) is between about 8:1 and about 4:1. In some embodiments, the first layer includes polycaprolactone (PCL), gelatin and alginate (AA), and the weight ratio of polycaprolactone (PCL), gelatin and alginate (AA) is between about 1:1:0.1 and about 1:1.85:0.125. In some embodiments, the first layer includes alginate (AA), and the weight percentage of alginate (AA) is between about 1 wt % and about 5 wt %.

In some embodiments, the second layer includes polycaprolactone (PCL) and hyaluronic acid (HA), and the weight ratio of polycaprolactone (PCL) to hyaluronic acid (HA) is between about 10:1 and about 35:1. In some embodiments, the second layer includes polycaprolactone (PCL) and polyvinyl alcohol (PVA), and the weight ratio of polycaprolactone (PCL) to polyvinyl alcohol (PVA) is between about 1:0.1 and about 1:0.16. In some embodiments, the second layer includes polycaprolactone (PCL), hyaluronic acid (HA) and polyvinyl alcohol (PVA), and the weight ratio of polycaprolactone (PCL), hyaluronic acid (HA) and polyvinyl alcohol (PVA) is between about 10:1:0.5 and about 35:1:1.

In some embodiments, the protective layer 14 is a single layer. For example, the protective layer 14 includes polycaprolactone (PCL), gelatin, hyaluronic acid (HA), alginate (AA), polyvinyl alcohol (PVA) or a combination thereof. In some embodiments, the protective layer 14 includes gelatin and alginate (AA). In some embodiments, the protective layer 14 includes gelatin. In some embodiments, the protective layer 14 includes gelatin and alginate (AA), and the weight ratio of gelatin to alginate (AA) is between about 4:1 and about 14.5:1. In some embodiments, the protective layer 14 includes gelatin, and the weight percentage of gelatin is between about 10 wt % and about 29.9 wt %.

In some embodiments, the grafting rate of polyethylene glycol dimethacrylate (PEGDMA) is between about 65% and about 72%. If the grafting rate is lower than the minimum percentage of the present disclosure, the effect of subsequent reactions with the photoinitiator may decrease, and even after the film is formed in the post process, the exposed amount of reactive functional groups is too small to effectively produce the reaction. Conversely, if the grafting rate is too high, one of the possible problems is the production of excess reactive functional groups, which will cause toxic reactions in subsequent clinical applications and cause inflammation in patients. The second is that the photocuring reaction is excessive, causing the light-cured layer to lose its softness and conformability when implanted into the human body in the future, or even produce a sharper corner to rub with the tissue, and then produce adverse reactions such as inflammation or tissue injury, causing pain after the patient has healed.

In some embodiments, the light-cured layer 12 and the protective layer 14 have an area ratio which is between about 5:100 and about 65:100. If the area of the protective layer 14 is fixed, the area ratio of the light-cured layer 12 to the protective layer 14 is too low, and the adhesion effect becomes poor and the purpose of preventing leakage cannot be achieved. If the area of the protective layer 14 is fixed, the area ratio of the light-cured layer 12 to the protective layer 14 is too high, which will affect the effect of the protective layer 14 in adsorbing tissue fluid (poor protection), causing the light-cured layer 12 to swell and warp. In some embodiments, when the area of the protective layer 14 is 100 $cm^2$, the light-cured layer 12 is 6.25 $cm^2$. In some embodiments, when the area of the protective layer 14 is 100 $cm^2$, the light-cured layer 12 is 64 $cm^2$.

In some embodiments, the protective layer 14 may be implemented independently.

The present disclosure aims at the film material with tissue attachment and water absorption (hydrophilic) (the light-cured layer—the first portion of the anti-curling film), using a protective manner (covered by the protective layer—the second portion of the anti-curling film) to produce a specific area ratio with the film material to limit the water absorption when the absorbent film is attached to the tissue surface (for example, liver, gastrointestinal tract, etc.). When the water-absorbent film is used clinically and attached to the surface of the internal organs of the body, it can effectively reduce the phenomenon of warping caused by the swelling of the volume of the water-absorbent film due to the absorption of a large amount of tissue fluid, and it can also effectively avoid the occurrence of detachment between the film material and the tissue surface due to warping.

The present disclosure is mainly to solve the warping condition caused by the water absorption of the film. The specific area ratio between the film layers (the light-cured layer 12 and the protective layer 14) is used to effectively control the water absorption state of the film and reduce the water absorption efficiency in the process of attaching to the tissue. Also, the design of light-sensitive curing is combined in the material. During the implementation, the UV light of a fixed wavelength is irradiated to strengthen the attachment effect of the film to the surface of the tissue, so that while the UV light promotes the attachment speed of the film, the polymer (as mentioned above, the polymer may be a film formed by the blending of PCL/PEGDMA or PLA/PEGDMA) of the light-cured layer rearranges the molecules under the condition of reducing water absorption, which reduces the generation of warping stress in the film, thereby eliminating the occurrence of warping.

Preparation Example 1

Preparation of Polyethylene Glycol Dimethacrylate (PEGDMA)

(1) 50 g of polyethylene glycol (PEG) (molecular weight: 8,000) was placed in a reaction tank and dissolved in 350 ml of tetrahydrofuran (THF). High-purity nitrogen was introduced to remove moisture. (2) Methacrylic anhydride (MA) was dissolved in 100 ml of tetrahydrofuran (THF) and slowly dropped into the above polyethylene glycol (PEG) solution. The ratio of polyethylene glycol (PEG) to methacrylic anhydride (MA) was 1:5. (3) Nitrogen was continuously introduced and the reaction temperature was maintained at 80° C. for 8 hours. Next, Ether (10 times larger than the original volume) was added for precipitation and purification, and then the precipitated sample was filtered. (4) The precipitated sample was re-dissolved in 60° C. and 100 ml of tetrahydrofuran (THF). After the above step (3) was performed, after the sample was filtered, the sample was dried in an extraction cabinet at the room temperature of 22° C. to 27° C. to obtain polyethylene glycol dimethacrylate (PEGDMA). The resulting polyethylene glycol dimethacrylate (PEGDMA) was analyzed by NMR. The signals of the double-bond structure of MA appeared at 5.57 ppm and 6.12 ppm on the NMR spectrum, which can confirm that polyethylene glycol (PEG) and methacrylic anhydride (MA) were synthesized to form polyethylene glycol dimethacrylate (PEGDMA). The yield was about 89.02%, and the synthetic grafting rate was about 68.45%.

Preparation Example 2

Preparation of a Light-Cured Layer

First, a solution (solution 1) containing 1 g of polycaprolactone (PCL) and 10 g of polyethylene glycol dimethacrylate (PEGDMA) was prepared. A solution (solution 2) containing 2 g of polylactic acid (PLA) and 2 g of polyethylene glycol dimethacrylate (PEGDMA) was prepared. Both the solution 1 and the solution 2 used dichloromethane (DCM) as the solvent. After the solution 1 and the solution 2 were prepared, an initiator 12959 was added to the two solutions respectively. The addition amount was 0.05 g and 0.01 g. The two solutions were completely dissolved in 16-24 hours.

Next, the solution 2 was coated on a Teflon flat substrate to form a film, and the coating thickness was set to 150 microns. After the film was formed, waiting for about 10 minutes, the solution 1 was poured onto the film formed by the solution 2 (i.e. the solution 2 was first coated to form a film, and then the solution 1 was coated and stacked to form a film on the film formed by the solution 2). The solution 1 was uniformly coated to form a film, and the thickness was set to 150 microns. After dichloromethane (DCM) was volatilized for 16 to 24 hours, a light-cured layer was obtained.

Preparation Example 3

Preparation of a Protective Layer

First, a solution containing 4 g of polycaprolactone (PCL) and a solution containing 0.5 g of alginate (AA) were prepared. PCL used dichloromethane (DCM) as the solvent. AA was dissolved in deionized water (DDW) in an oven at 50° C. After the respective preparation was completed, the two were mixed, stirred and emulsified to complete the preparation of solution 1.

A solution containing 4 g of polycaprolactone (PCL) and a solution containing 0.1 g of polyvinyl alcohol (PVA) were prepared. PCL used dichloromethane (DCM) as the solvent. PVA was dissolved in deionized water (DDW) in an oven at 50° C. After the respective preparation was completed, the two were mixed, stirred and emulsified to complete the preparation of solution 2.

Next, the solution 2 was coated on a Teflon flat substrate to form a film, and the coating thickness was set to 150 microns. After the film was formed, waiting for about 10 minutes, the solution 1 was poured onto the film formed by the solution 2 (i.e. the solution 2 was first coated to form a film, and then the solution 1 was coated and stacked to form a film on the film formed by the solution 2). The solution 1 was uniformly coated to form a film, and the thickness was set to 150 microns. After dichloromethane (DCM) was volatilized for 16 to 24 hours, a protective layer was obtained.

Preparation Example 4

Preparation of an Anti-Curling Film

The preparation of an anti-curling film was mainly to coat the light-cured layer of Preparation Example 2 on the protective layer containing polycaprolactone (PCL), gelatin, hyaluronic acid (HA), etc., so that the protective layer and the light-cured layer were combined to form the same film. The coating sequence was to prepare the protective layer first, and then apply the light-cured layer on the protective layer according to the steps of Preparation Example 2. After the solvent was evaporated for 16 to 24 hours, an anti-curling film was obtained.

Example 1

Figure 3:
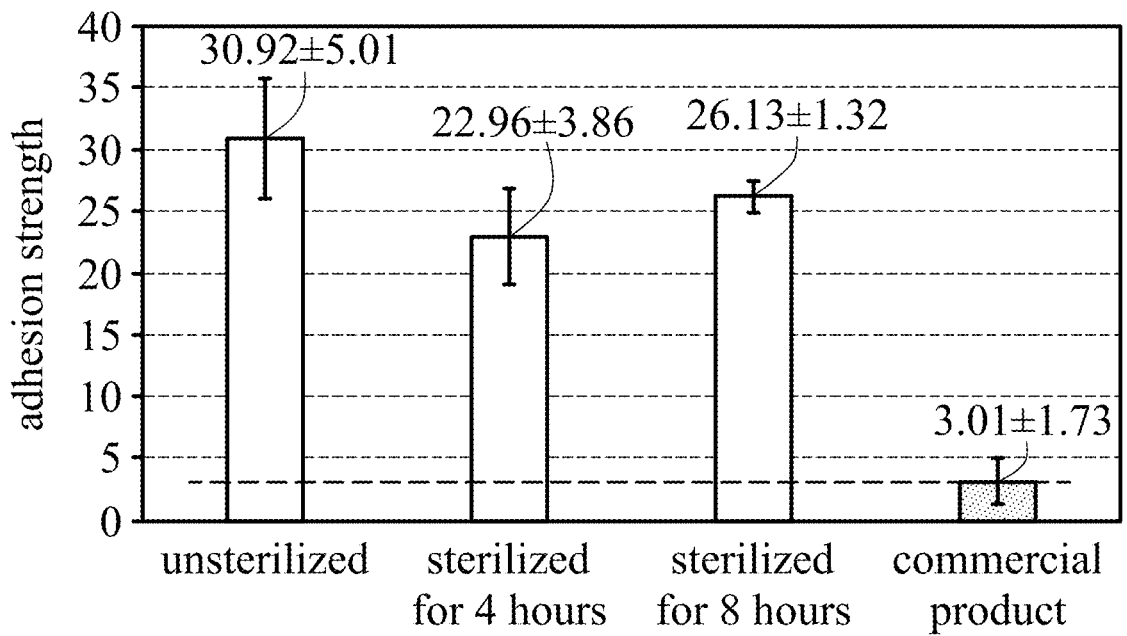
FIG. 3 shows a test analysis (ASTM F2258) of adhesion strength of a light-cured layer (attached to pig intestines) before and after sterilization in accordance with one embodiment of the present disclosure.
Figure 4:
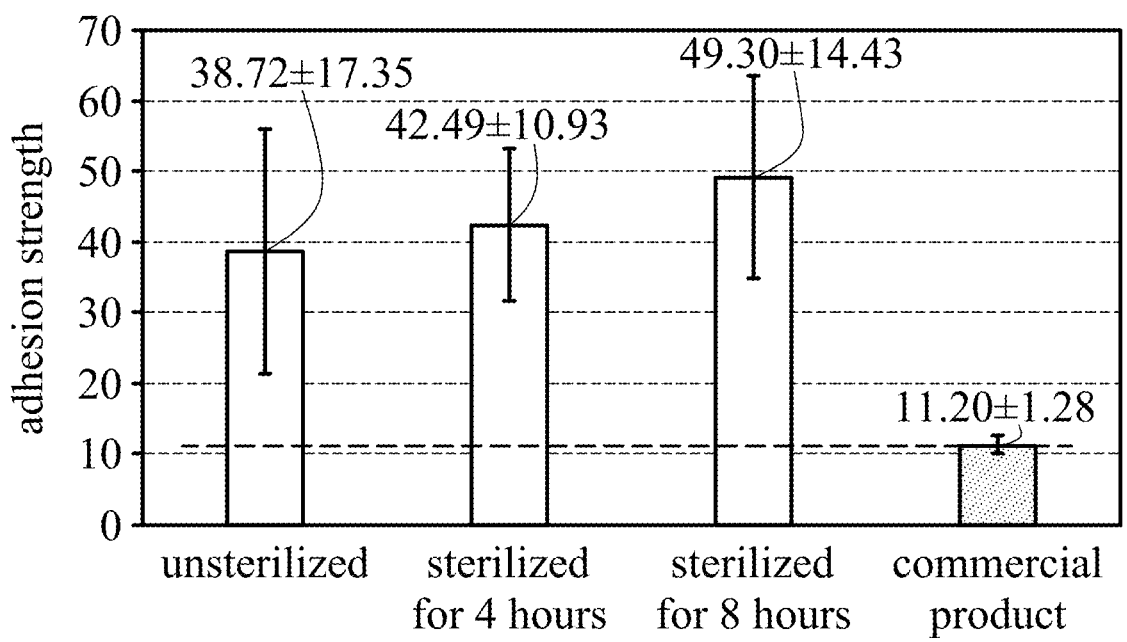
FIG. 4 shows a test analysis (ASTM F2255) of adhesion strength of a light-cured layer (attached to pig intestines) before and after sterilization in accordance with one embodiment of the present disclosure.

Test Analysis of Adhesion Strength of a Light-Cured Layer (Attached to Pig Intestines) Before and After Sterilization First, according to the clinical aseptic requirements, a light-cured layer was sterilized with ethylene oxide (EO). After sterilization, according to the requirements of ASTM F2258 and ASTM F2255, a test analysis for in-vitro tissue attachment of samples was performed. Before analysis, according to the size and operation method required by ASTM, the light-cured layer was cut and attached to the mold and the intestinal tissue respectively. At the distance of 1 cm above the light-cured layer, UV light was irradiated for 10 minutes continuously, and the intensity of the light source was recorded every minute. The intensity of UV light decreased from 600 mW to 520 mW. The wavelength of UV light used was 365 nm (the wavelength range of UV light required for photocuring is 270-400 nm). After the UV-light irradiation for 60 seconds, the attachment test analysis was performed. The analysis results of ASTM F2258 are shown in FIG. 3. The commercially available product was Tissue-Patch™ from Tissuemed. The original specification was 10*10 cm, and the thickness was about 40 µm. The size used to analyze the adhesion strength was the same as the samples of this example, and all were cut according to the requirements of ASTM. The adhesive strengths of unsterilized, sterilized for 4 hours, sterilized for 8 hours, and the commercially available TissuePatch™ were 30.92±5.01 mJ, 22.96±3.86 mJ, 26.13±1.32 mJ, 3.01±1.73 mJ, respectively. The analysis results of ASTM F2255 are shown in FIG. 4. The adhesive strengths of unsterilized, sterilized for 4 hours, sterilized for 8 hours, and the commercially available product were 38.72±17.35 mJ, 42.49±10.93 mJ, 49.30±14.43 mJ, 11.20±1.28 mJ, respectively.

Example 2

Figure 5:
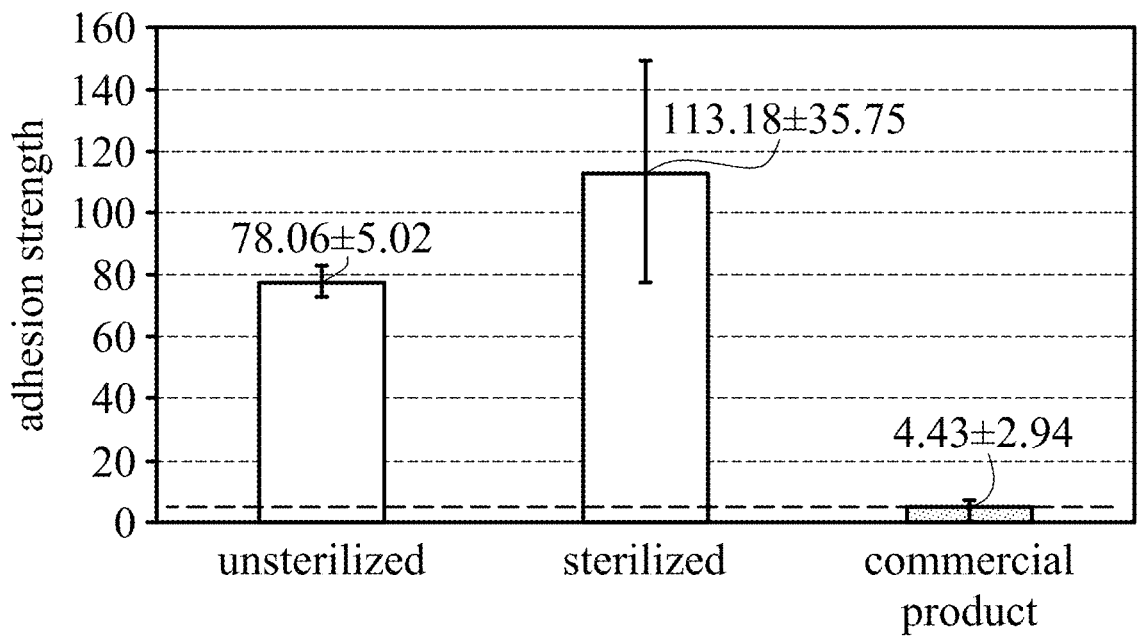
FIG. 5 shows a test analysis (ASTM F2258) of adhesion strength of a light-cured layer (attached to pig liver) before and after sterilization in accordance with one embodiment of the present disclosure.
Figure 6:
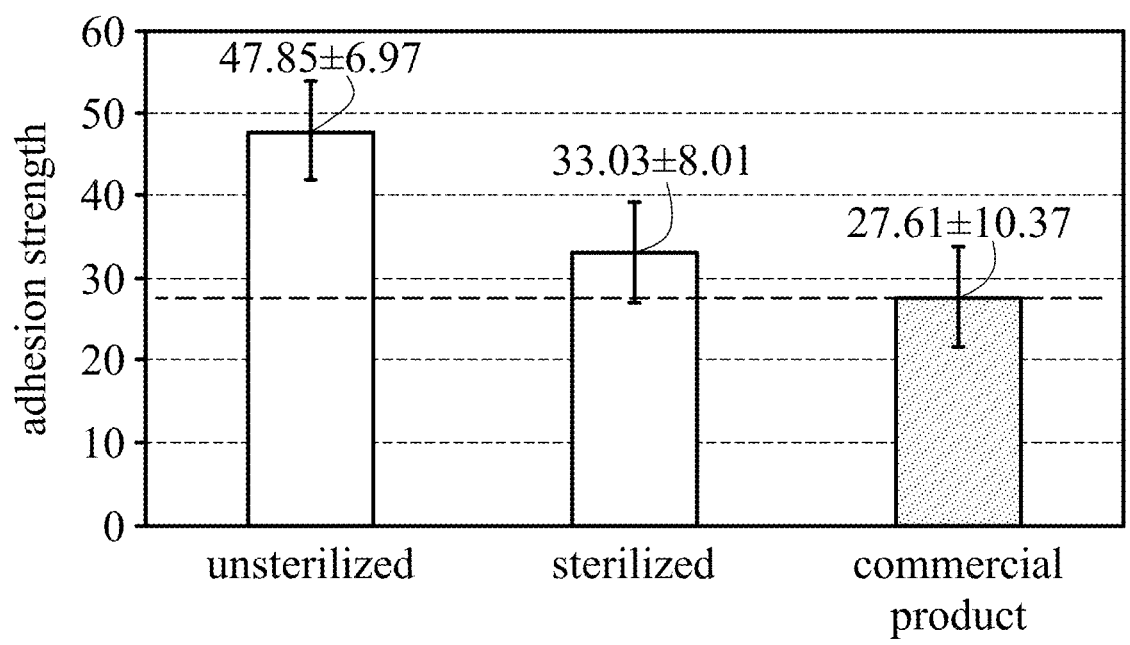
FIG. 6 shows a test analysis (ASTM F2255) of adhesion strength of a light-cured layer (attached to pig liver) before and after sterilization in accordance with one embodiment of the present disclosure.

Test Analysis of Adhesion Strength of a Light-Cured Layer (Attached to Pig Liver) Before and After Sterilization First, according to the clinical aseptic requirements, a light-cured layer was sterilized with ethylene oxide (EU). After sterilization, according to the requirements of ASTM F2258 and ASTM F2255, a test analysis for in-vitro tissue attachment of samples was performed. Before analysis, the light-cured layer was attached to the liver. The attachment size was the same as the above-mentioned Example 1, and the size and operation method were implemented according to the requirements of the ASTM text. At the distance of 1 cm above the light-cured layer, UV light was irradiated for 10 minutes continuously, and the intensity of the light source was recorded every minute. The intensity of UV light decreased from 600 mW to 520 mW. After the UV-light irradiation for 60 seconds, the attachment test analysis was performed. The analysis results of ASTM F2258 are shown in FIG. 5. Tested with unsterilized, sterilized, and the commercially available product (TissuePatch™), the adhesion strengths were 78.06±5.02 mJ, 113.18±35.75 mJ, 4.43±2.94 mJ, respectively. The analysis results of ASTM F2255 are shown in FIG. 6. The adhesive strengths of unsterilized, sterilized, and the commercially available product were 47.85±6.97 mJ, 33.03±8.01 mJ, 27.61±10.37 mJ, respectively.

Example 3

Test Analysis of Adhesion Strength of an Anti-Curling Film (Attached to Pig Intestines)

Figure 7:
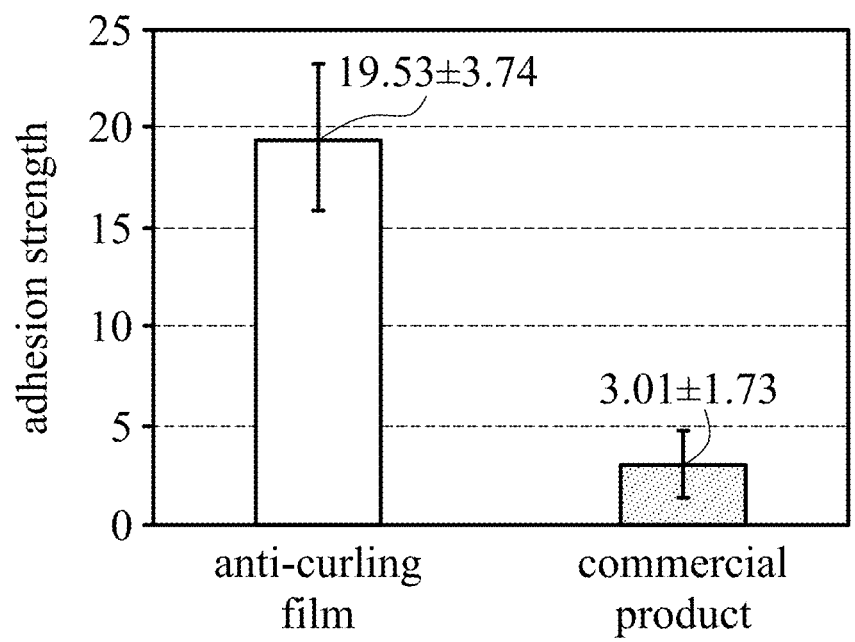
FIG. 7 shows a test analysis (ASTM F2258) of adhesion strength of an anti-curling film (attached to pig intestines) before and after sterilization in accordance with one embodiment of the present disclosure.
Figure 8:
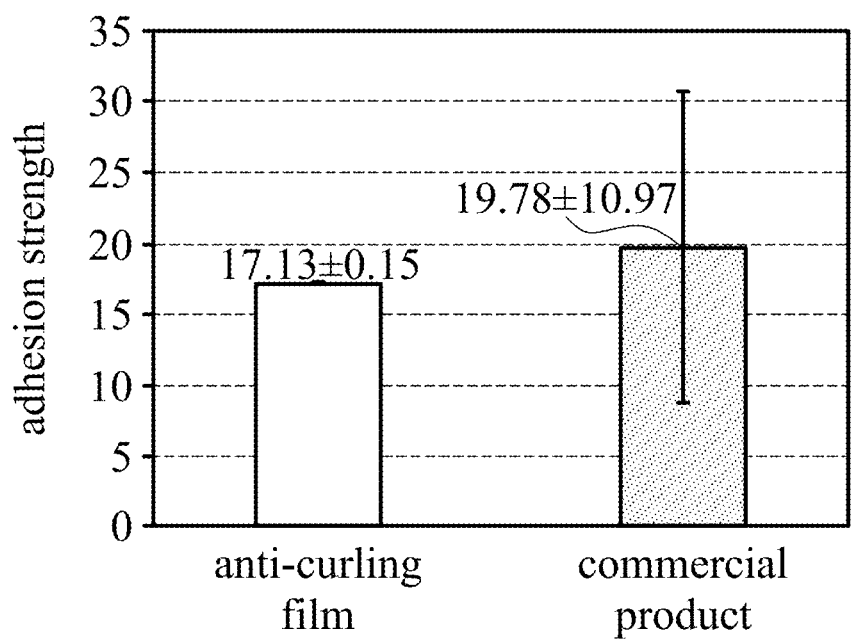
FIG. 8 shows a test analysis (ASTM F2255) of adhesion strength of an anti-curling film (attached to pig intestines) before and after sterilization in accordance with one embodiment of the present disclosure.

According to the requirements of ASTM F2258 and ASTM F2255, a test analysis for in-vitro tissue attachment of the anti-curling film prepared in Preparation Example 4 was performed. Before analysis, the anti-curling film was attached to the intestinal tissue. At the distance of 1 cm above the anti-curling film, UV light was irradiated for 10 minutes continuously, and the intensity of the light source was recorded every minute. The intensity of UV light decreased from 600 mW to 520 mW. After the UV-light irradiation for 60 seconds, the attachment test analysis was performed. The analysis results of ASTM F2258 are shown in FIG. 7. The adhesion strengths of the anti-curling film prepared in Preparation Example 3 and the commercially available TissuePatch™ were 19.53±3.74 mJ and 3.01±1.73 mJ, respectively. The analysis results of ASTM F2255 are shown in FIG. 8. The adhesion strengths of the anti-curling film prepared in Preparation Example 4 and the commercially available product were 17.13±0.15 mJ and 19.78±10.97 mJ, respectively. From the above analysis results, it can be seen that the adhesion strength of the anti-curling film of the present disclosure is stable and better than that of the commercially available products.

Example 4

Test Analysis of Water Swelling of a Light-Cured Layer (Attached to Pig Liver)

Figure 9:
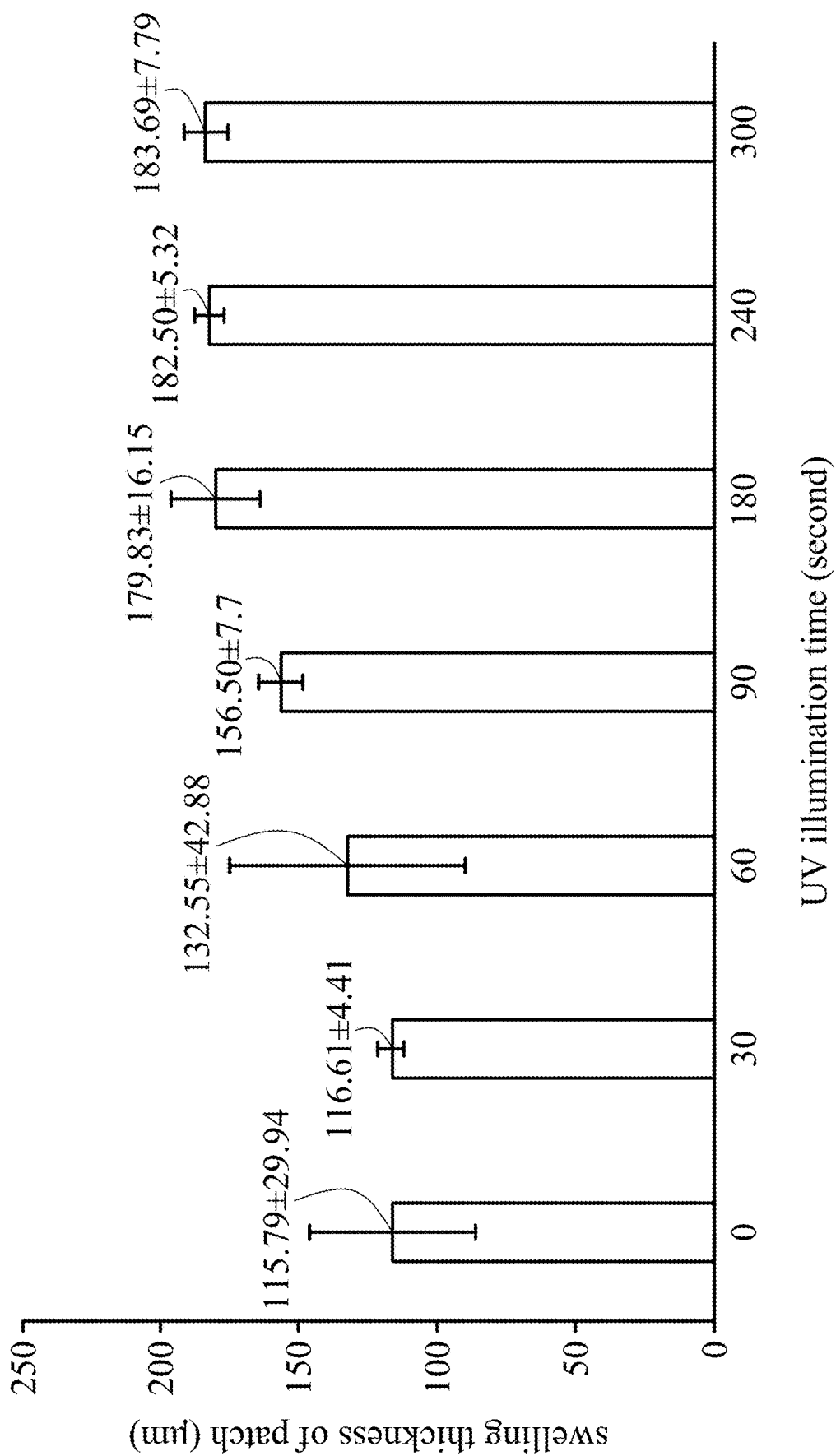
FIG. 9 shows a test analysis of water swelling of a light-cured layer (attached to pig liver) in accordance with one embodiment of the present disclosure.
Figure 10:
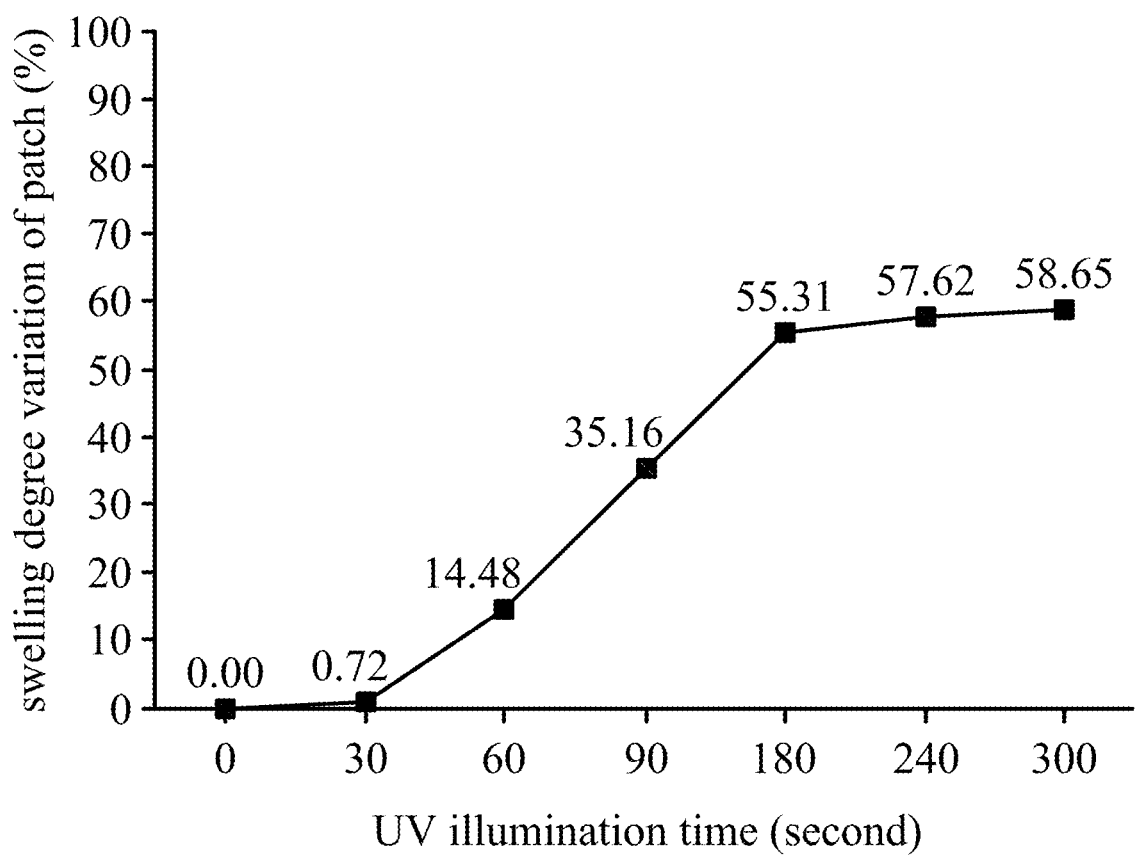
FIG. 10 shows an analysis of swelling degree of a light-cured layer (attached to pig liver) in accordance with one embodiment of the present disclosure.

A light-cured layer (test size was 2.5*2.5 cm and 8*8 cm respectively) was attached to the liver, and continuously irradiated and cured with UV light. The irradiation time was 30 seconds, 60 seconds, 90 seconds, 180 seconds, 240 seconds and 300 seconds. After the irradiation was completed, a fixed volume of 200 microliters (µL) of normal saline was given for water swelling test. After the same water absorption time, 30 minutes later, the swelling thickness of the light-cured layer was observed by a microscope. The analysis results are shown in FIG. 9. It can be seen from FIG. 9 that after the UV light irradiation for 180 seconds, the thickness of the light-cured layer reached equilibrium and no longer increased significantly. There was little change in thickness when irradiated for 300 seconds. The swelling degree (percentage) was calculated (Wt−W0/W0*100=swelling degree (%), Wt: weight after swelling, W0: weight before swelling). The obtained swelling degree (percentage) curve is shown in FIG. 10. It can be seen from FIG. 10 that the swelling degree of the photo-cured layer was about 55.31 to 58.65% of the original thickness after 180 to 300 seconds of illumination. After 180 seconds of illumination, the change slowed down significantly. It can also be verified that UV light can make the swelling stabilization time of the photo-cured layer at least 180 seconds.

Example 5

Test Analysis of Water Swelling of an Anti-Curling Film (Attached to Pig Liver)

The following is a test analysis of water swelling for the anti-curling film prepared in Preparation Example 4. The test was divided into a control group (without a protective layer) and an experimental group (with a protective layer). The sample of the control group was attached to the liver, irradiated with UV light for 60 seconds and immersed in saline for 30 minutes. Because the sample was not protected by a protective layer, the sample was warped and detached from the surface of the tissue. The experiment group was divided into a first experiment group and a second experiment group. In the anti-curling film used in the first experiment group, the area of the protective layer was 10 cm×10 cm, and the area of the light-cured layer was 2.5 cm×2.5 cm. In the anti-curling film used in the second experiment group, the area of the protective layer was 10 cm×10 cm, and the area of the light-cured layer was 8 cm×8 cm. The anti-curling film was attached to the liver and irradiated with UV light. The irradiation time was 60 seconds, 180 seconds, and 300 seconds, respectively. After the irradiation was completed, the liver tissue was immersed in saline for 16-18 hours. It can be seen from the test results that the sample of the first experiment group was not warped or fallen off after being exposed to UV light for 180 seconds and immersed for a long time of 16 to 18 hours. Similarly, the sample of the second experiment group was not curled or fallen off after being exposed to UV light for 60 seconds and immersed for a long time of 16 to 18 hours. The above test results verify that, under the effective protection of the protective layer (the area of the light-cured layer accounted for 6.25% to 64% of the area of the protective layer), the light-cured layer can effectively eliminate the warping of the film due to water absorption.

Example 6

Cytotoxicity (Biocompatibility) Analysis of an Anti-Curling Film

According to ISO 10993-5, the cytotoxicity analysis of the anti-curling film prepared in Preparation Example 4 was performed below. The film was placed in Dulbecco's modified Minimal Essential Medium (DMEM) containing 10% fetal bovine serum (FBS) for extraction at 37° C. After 24 hours, the extract was co-cultured with L929 fibroblasts. Co-cultivation time was 24 hours. The cell survival rate of L929 fibroblasts co-cultured with the sample extract was greater than 70%, indicating that the anti-curling film disclosed in the present disclosure has no toxicity and good biocompatibility.

Example 7

Implantation Test of an Anti-Curling Film in Rabbit Body (Attached to Liver)

The following is the verification of the efficacy of the anti-curling film implanted in the rabbit body. The test was divided into a control group (without a protective layer) and an experimental group (with a protective layer). In the control group, the area of the light-cured layer used was 1.5 cm×1.5 cm. In the anti-curling film used in the experiment group, the area of the protective layer was 2.5 cm×2.5 cm, and the area of the light-cured layer was 1.5 cm×1.5 cm. After the samples of the two groups were irradiated with UV light for 180 seconds at the same time, the response of the patches was observed respectively. At this time, the sample of the control group was obviously warped, and it was partially separated from the surface of the tissue. After suturing, waiting for 48 hours, the samples were taken and observed. It can be seen from the results that the patch of the control group was slightly sticky. Although it still existed at the site of the surgical liver, the patch was folded due to warping. In contrast, the patch of the experimental group had no adhesion phenomenon, and was stably attached to the surface of the liver without any warping or detachment.

Example 8

Implantation Test of an Anti-Curling Film in Pig Body (Attached to Intestines)

The following is the verification of the efficacy of the anti-curling film implanted in the pig body. In the first step, the intestinal injury was positioned. In the second step, the anti-curling film was taken in a sterile manner. In the third step, the film was warped and the anti-curling film was delivered into the body using minimally invasive surgical instruments. In the fourth step, the film was attached to the wound and to cover the wound completely. In the fifth step, a light source with a specific UV-light wavelength was used for irradiation. In the sixth step, the illumination time was 180 seconds. After the above six steps were completed, according to general clinical postoperative operation methods, the minimally invasive wound on the abdomen was sutured and disinfected. After one month, the samples were taken and observed.

The animal was sacrificed for sampling after one month. Before sacrifice, the wound was observed by the endoscope used for minimally invasive surgery. The observation results showed that the anti-curling film did not produce adverse reactions such as adhering on the intestinal wound after one month. A faint trace of the film above the wound was observed. Based on this, it can be determined that the anti-curling film can be stably attached to the intestinal wound without warping and other adverse reactions. From the above results, it can be proved that the anti-curling film of the present disclosure can not only effectively solve the problem of patch warping caused by water swelling after the clinically commonly used water-absorbing patch film is implanted in the body, but also avoid other possible sequelae.

Example 9

Implantation Test of an Anti-Curling Film in Pig Body (Attached to Intestines, Stomach, Liver) (Observed by Appearance)

The following is the verification of the efficacy of the anti-curling film implanted in the pig body for a period of one and three months. The organs implanted with the film were intestine, stomach and liver. The samples were sampled and observed after one month and three months respectively. One month later, after sampling and observation, it can be found that there was no adhesion or leakage in the various organs. Three months later, after sampling and observation, it can be found that the appearance of the intestines was normal, while a little adhesive tissue occurred on the stomach and liver. During the sampling process, the proliferative tissues that adhere to the stomach can be separated without intervention of external force. The postoperative adhesion was a normal reaction, and it was not a clinically undesirable adhesion situation. The adhesion condition in the liver was relieved by just flicking. Since the liver is an organ that is easy to be adhered, any surgical operation may cause adhesion. Whether it is caused by the anti-curling film, it is still necessary to determine the result clearly by section analysis. In summary, in the performance of the adhesion index, the anti-curling film disclosed in the present disclosure has the best effect on the intestinal organs. The stomach and liver can still be candidate organs and application locations for future clinical indications.

Example 10

Implantation Test of an Anti-Curling Film in Pig Body (Attached to Intestines, Stomach, Liver) (Observed by Tissue Staining)

Figure 11:
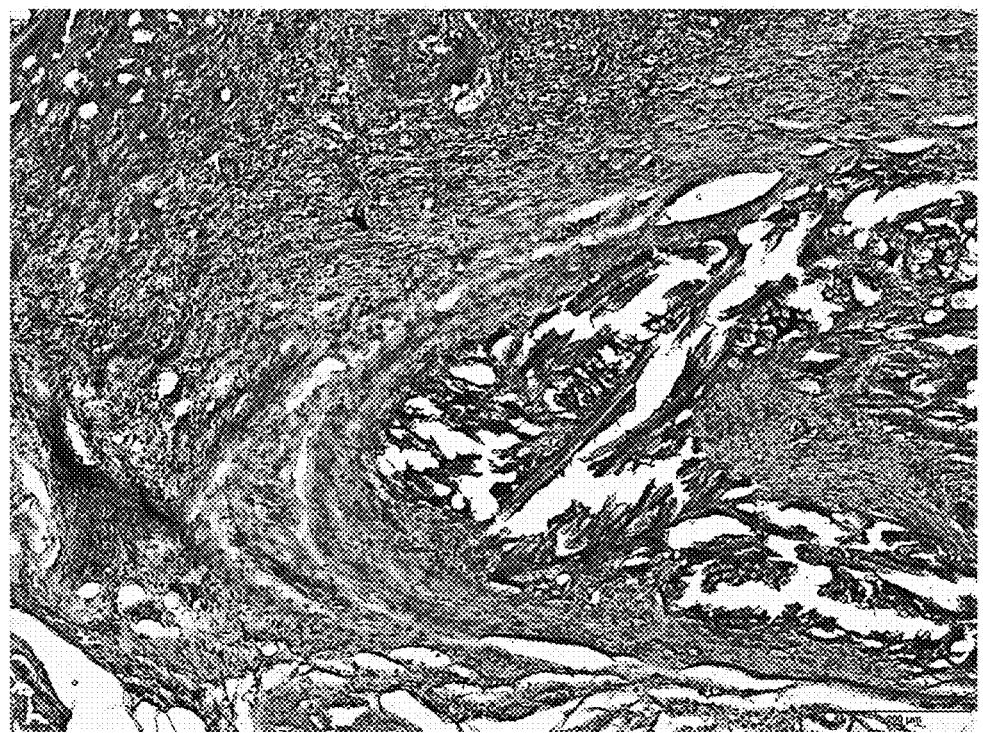
FIG. 11 shows the H&E staining results of intestinal tissue sections in accordance with one embodiment of the present disclosure.
Figure 12:
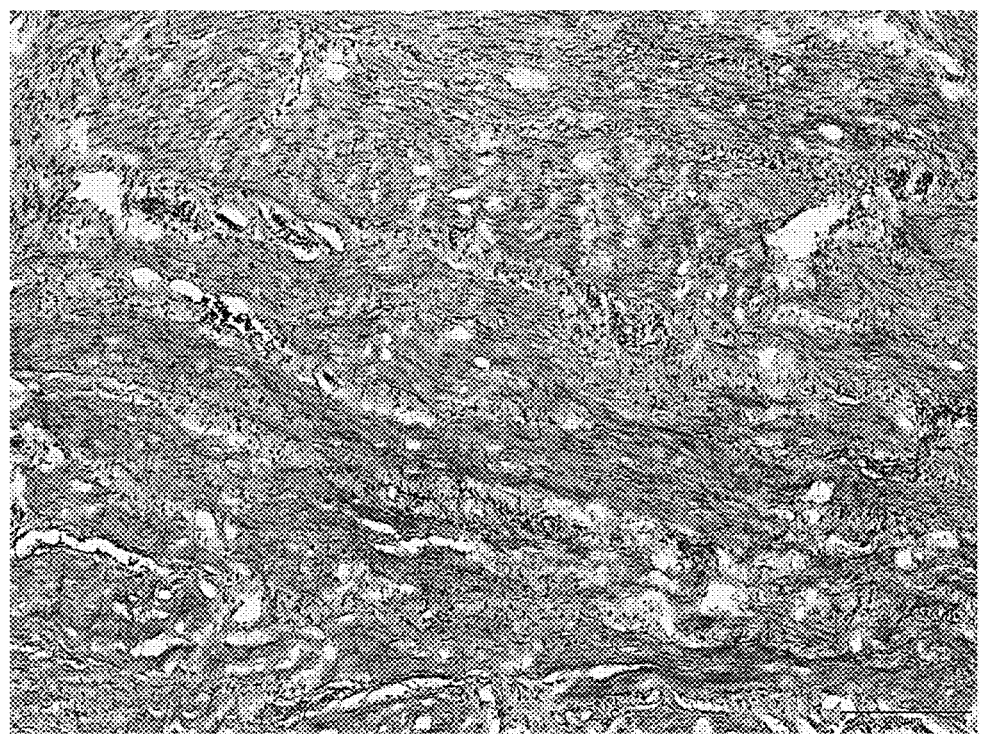
FIG. 12 shows the H&E staining results of stomach tissue sections in accordance with one embodiment of the present disclosure.
Figure 13:
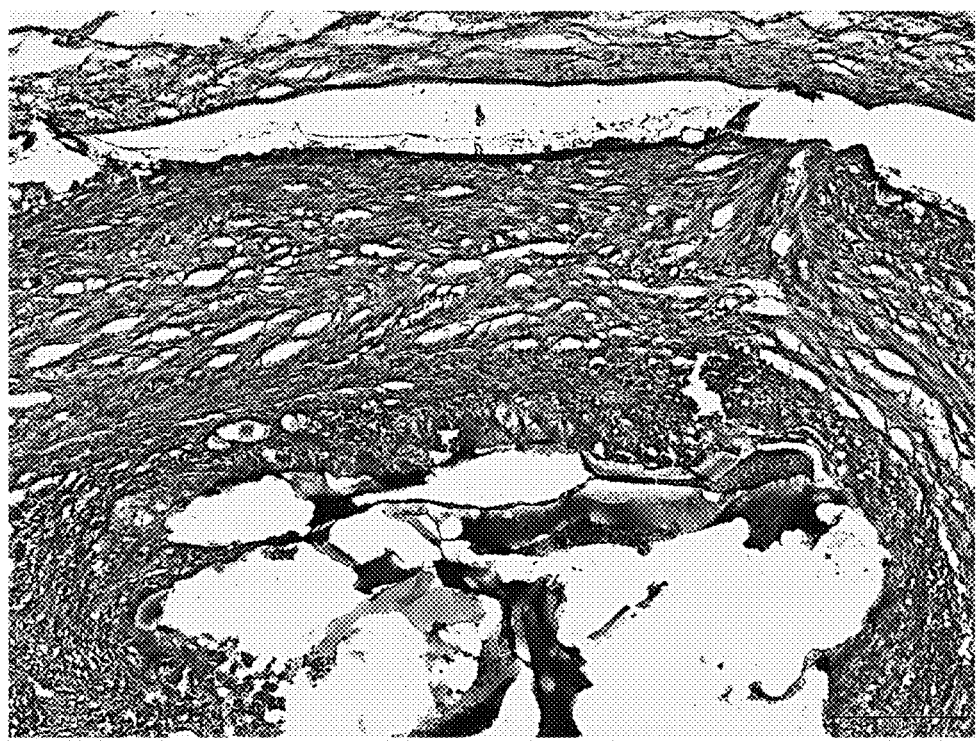
FIG. 13 shows the H&E staining results of liver tissue sections in accordance with one embodiment of the present disclosure.

In this example, the samples were taken one month later, and the tissues were sectioned and stained for observation. The staining of the intestine, stomach and liver was performed, including H&E (hematoxylin and eosin stain), MGT (Masson's Trichrome Stain) and staining of CD45 inflammation of immunohistochemistry (IHC). The H&E staining result (as shown in FIG. 11) of the intestinal tissue section showed that the wound was effectively covered by the material, and the wound was repaired to achieve a sealing effect, which is consistent with the appearance observed at the time of sampling. The H&E staining result (as shown in FIG. 12) of the gastric tissue section is the same as that of the intestinal tissue. The wound was completely covered by the material, and the wound tissue was also repaired, which is consistent with the appearance observed at the time of sampling. There was no leakage or adhesion and proliferation of tissue. The H&E staining result (as shown in FIG. 13) of the liver tissue section showed that the film can still exist stably on the tissue surface (since the liver was not easy to stop bleeding, in order to avoid multiple variables affecting the experiment, only the film was implanted in the body to attach, and no wound was created). Through H&E staining observation, it can be found that the light-cured patch can stably exist on the surface of the tissue, and can accurately and stably seal the postoperative wound to stop leakage (no sutures were used to fix the patch or repair the wound). This verifies the effectiveness of the light-cured patch to prevent leakage. In addition, the upper part of the film was observed from the tissue section, and no adverse hyperplastic tissue was observed, which is consistent with the appearance observed at the time of sampling, and also verified the anti-adhesion effect of the light-cured patch.

Figure 14:
FIG. 14 shows the MGT staining results of intestinal tissue sections in accordance with one embodiment of the present disclosure.
Figure 15:
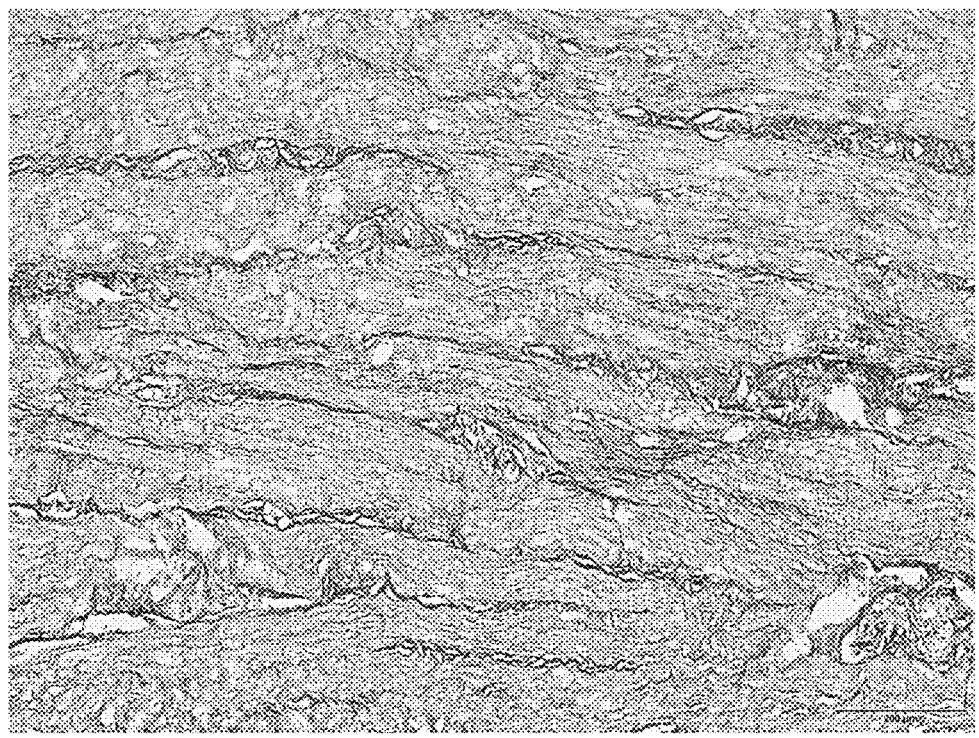
FIG. 15 shows the MGT staining results of stomach tissue sections in accordance with one embodiment of the present disclosure.
Figure 16:
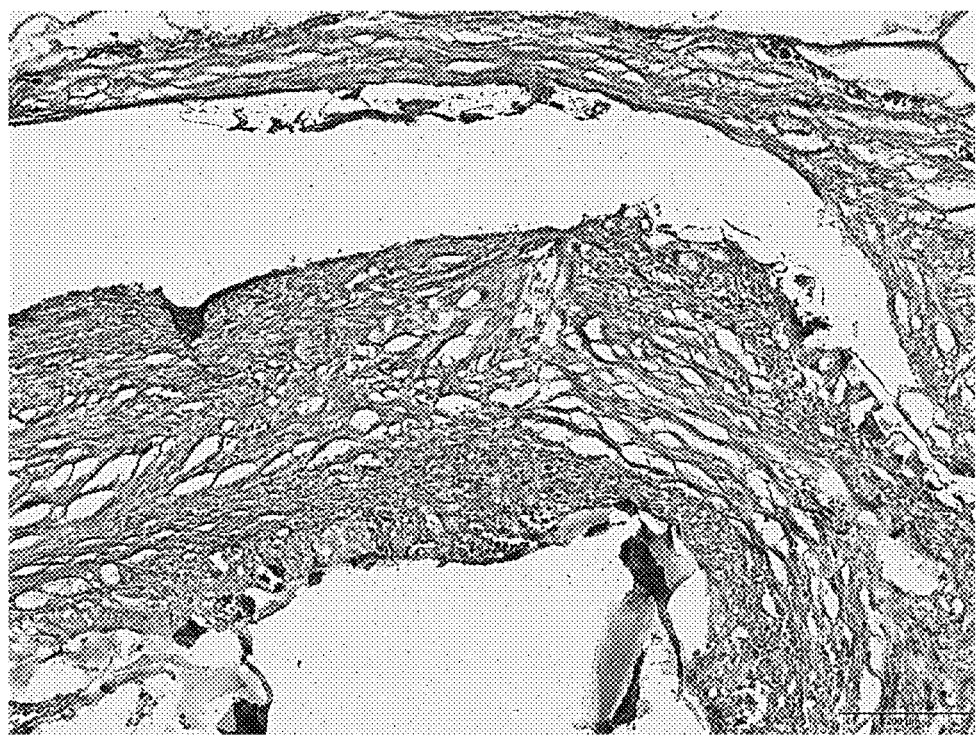
FIG. 16 shows the MGT staining results of liver tissue sections in accordance with one embodiment of the present disclosure.

In order to verify the efficacy of the light-cured patch and the state of tissue repair, the MGT staining was performed on the above-mentioned tissues. In the MGT staining, the collagen produced by the connective tissue was mainly observed. The states of tissue sections of the intestine (as shown in FIG. 14), stomach (as shown in FIG. 15), and liver (as shown in FIG. 16) were observed by the MGT staining. The results are shown in the 100× photos, the blue-green collagen appeared in the wound. This means that after the wound was sealed by the light-cured patch to prevent leakage, the film was used as a repair bridge, allowing fibroblasts to repair defects between wounds along the material, and then produce extracellular matrix collagen. It can also be observed that the material was surrounded by blue-green connective tissue, and the material appeared damaged. This phenomenon can be inferred that the material begins to degrade after being coated by the tissue.

After the section analysis of H&E and MGT was completed, the CD45 staining of immunohistochemistry (IHC) was performed on the tissues of the intestine, stomach and liver. IHC uses the specific binding between antibodies and antigens to detect the expression and location of target proteins in tissues or cells. CD45 is dyed brown (DAB) for identification, and hematoxylin is used to stain the nucleus for identification. CD45 is present on all white blood cells and is also known to help identify all hematopoietic cells except mature red blood cells and platelets. The following describes the results presented by CD45 in the three organs of the intestine, stomach and liver under a 10× microscope. Under the 10× field of view, the observation results showed that only obvious brown (DAB) precipitated immune response appeared around the material, and there was no significant immune inflammatory response at the wounds of the intestine and stomach. The inflammatory response was further observed under 100× and 400× microscopes. The results showed that under 100×, only the intestinal tract had a slight inflammatory response, while other organs did not show a serious immune response. This means that one month after the light-cured patch was implanted, after the acute inflammation period in the first two weeks, the tissue had begun to enter the repair phase (M2 phase).

Based on the above analysis, the performance of the anti-curling film of the present disclosure after being implanted in the body meets the expected leak-stop effect, and there is no adverse reaction of adhesion. According to the analysis results of the tissue sections, one month after implantation in the body, the tissue has begun to be repaired, and the efficacy verification in large animals is quite successful.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An anti-curling film, comprising:
a first portion comprising polylactic acid (PLA), polycaprolactone (PCL), polyethylene glycol dimethacrylate (PEGDMA) and a photoinitiator; and
a second portion covering the first portion, wherein the second portion comprises polycaprolactone (PCL), gelatin, hyaluronic acid (HA), alginate (AA), polyvinyl alcohol (PVA) or a combination thereof.

2. The anti-curling film as claimed in claim 1, wherein polyethylene glycol dimethacrylate (PEGDMA) has a grafting rate which is between 65% and 72%.

3. The anti-curling film as claimed in claim 1, wherein polylactic acid (PLA), polycaprolactone (PCL) and polyethylene glycol dimethacrylate (PEGDMA) have a weight ratio which is between 0.5:1:1 and 0.5:1:6.

4. The anti-curling film as claimed in claim 1, wherein the first portion comprises a first layer and a second layer.

5. The anti-curling film as claimed in claim 4, wherein the first layer comprises polycaprolactone (PCL) and polyethylene glycol dimethacrylate (PEGDMA), and polycaprolactone (PCL) and polyethylene glycol dimethacrylate (PEGDMA) have a weight ratio which is between 1:6 and 1:12.

6. The anti-curling film as claimed in claim 4, wherein the second layer comprises polyethylene glycol dimethacrylate (PEGDMA) and polylactic acid (PLA), and polyethylene glycol dimethacrylate (PEGDMA) and polylactic acid (PLA) have a weight ratio which is between 1:1 and 3:1.

7. The anti-curling film as claimed in claim 1, wherein polyethylene glycol dimethacrylate (PEGDMA), polylactic acid (PLA) and the photoinitiator have a weight ratio which is between 1:1:0.005 and 3:1:0.015.

8. The anti-curling film as claimed in claim 1, wherein polylactic acid (PLA), polycaprolactone (PCL), polyethylene glycol dimethacrylate (PEGDMA) and the photoinitiator have a weight ratio which is between 2:1:7:0.03 and 3:1:12:0.06.

9. The anti-curling film as claimed in claim 1, wherein the second portion comprises a first layer and a second layer.

10. The anti-curling film as claimed in claim 9, wherein the first layer comprises polycaprolactone (PCL), gelatin, alginate (AA) or a combination thereof.

11. The anti-curling film as claimed in claim 9, wherein the second layer comprises polycaprolactone (PCL), hyaluronic acid (HA), polyvinyl alcohol (PVA) or a combination thereof.

12. The anti-curling film as claimed in claim 10, wherein the first layer comprises polycaprolactone (PCL) and gelatin, and polycaprolactone (PCL) and gelatin have a weight ratio which is between 0.14:1 and 1:1.

13. The anti-curling film as claimed in claim 10, wherein the first layer comprises polycaprolactone (PCL) and alginate (AA), and polycaprolactone (PCL) and alginate (AA) have a weight ratio which is between 8:1 and 4:1.

14. The anti-curling film as claimed in claim 10, wherein the first layer comprises polycaprolactone (PCL), gelatin and alginate (AA), and polycaprolactone (PCL), gelatin and alginate (AA) have a weight ratio which is between 1:1:0.1 and 1:1.85:0.125.

15. The anti-curling film as claimed in claim 10, wherein the first layer comprises alginate (AA), and alginate (AA) has a weight percentage which is between 1 wt % and 5 wt %.

16. The anti-curling film as claimed in claim 11, wherein the second layer comprises polycaprolactone (PCL) and hyaluronic acid (HA), and polycaprolactone (PCL) and hyaluronic acid (HA) have a weight ratio which is between 10:1 and 35:1.

17. The anti-curling film as claimed in claim 11, wherein the second layer comprises polycaprolactone (PCL) and polyvinyl alcohol (PVA), and polycaprolactone (PCL) and polyvinyl alcohol (PVA) have a weight ratio which is between 1:0.1 and 1:0.16.

18. The anti-curling film as claimed in claim 11, wherein the second layer comprises polycaprolactone (PCL), hyaluronic acid (HA) and polyvinyl alcohol (PVA), and polycaprolactone (PCL), hyaluronic acid (HA) and polyvinyl alcohol (PVA) have a weight ratio which is between 10:1:0.5 and 35:1:1.

19. The anti-curling film as claimed in claim 1, wherein the second portion comprises gelatin and alginate (AA), or gelatin.

20. The anti-curling film as claimed in claim 19, wherein the second portion comprises gelatin and alginate (AA), and gelatin and alginate (AA) have a weight ratio which is between 4:1 and 14.5:1.

21. The anti-curling film as claimed in claim 19, wherein the second portion comprises gelatin, and gelatin has a weight percentage which is between 10 wt % and 29.9 wt %.

22. The anti-curling film as claimed in claim 1, wherein the first portion and the second portion have an area ratio which is between 5:100 and 65:100.

23. An anti-curling film, comprising: the second portion of the anti-curling film as claimed in claim 1.

* * * * *